(12) United States Patent
Traxler et al.

(10) Patent No.: US 9,194,831 B2
(45) Date of Patent: Nov. 24, 2015

(54) THERMOGRAPHIC TEST METHOD AND TESTING DEVICE FOR CARRYING OUT THE TEST METHOD

(75) Inventors: Gerhard Traxler, Vienna (AT); Werner Palfinger, Vienna (AT)

(73) Assignee: Institut Dr. Foerster GmbH & Co. KG, Reutlingen (DE)

( * ) Notice: Subject to any disclaimer, the term of this patent is extended or adjusted under 35 U.S.C. 154(b) by 533 days.

(21) Appl. No.: 13/639,354

(22) PCT Filed: Apr. 7, 2011

(86) PCT No.: PCT/EP2011/055386
§ 371 (c)(1),
(2), (4) Date: Dec. 12, 2012

(87) PCT Pub. No.: WO2011/124628
PCT Pub. Date: Oct. 13, 2011

(65) Prior Publication Data
US 2013/0077650 A1 Mar. 28, 2013

(30) Foreign Application Priority Data
Apr. 8, 2010 (EP) .................................... 10003756

(51) Int. Cl.
*G01N 25/72* (2006.01)
*G06T 7/00* (2006.01)

(52) U.S. Cl.
CPC .............. *G01N 25/72* (2013.01); *G06T 7/0004* (2013.01); *G06T 2207/10048* (2013.01); *G06T 2207/30136* (2013.01)

(58) Field of Classification Search
CPC ................. G01N 25/72; G06T 7/0004; G06T 2207/30136; G06T 2207/10048

USPC ............................................................. 374/5
See application file for complete search history.

(56) References Cited

U.S. PATENT DOCUMENTS 6,000,844 A 12/1999 Cramer et al.
6,461,035 B2 10/2002 Meinlschmidt et al.
(Continued)

FOREIGN PATENT DOCUMENTS

CN 1292871 A 4/2001
CN 1696674 A 11/2005
(Continued)

OTHER PUBLICATIONS

Japanese Office Action dated Aug. 18, 2014 with English translation (five pages).
(Continued)

*Primary Examiner* — Lisa Caputo
*Assistant Examiner* — Philip Cotey
(74) *Attorney, Agent, or Firm* — Crowell & Moring LLP (57) ABSTRACT

A thermographic test method locally resolves detection and identification of defects near the surface in a test object. A surface area of the test object is heated up. A series of thermographic images following one after another at a time interval is recorded within a heat propagation phase, each image representing a local temperature distribution in a surface region of the test object recorded by the image. Positionally correctly assigned temperature profiles are determined from the images, each positionally correctly assigned temperature profile being assigned to the same measuring region of the test object surface. Variations over time of temperature values are determined from the temperature profiles for a large number of measuring positions of the measuring region. These variations are evaluated on the basis of at least one evaluation criterion indicative of the heat flow in the measuring region.

15 Claims, 6 Drawing Sheets

(56) References Cited

U.S. PATENT DOCUMENTS

| | | | |
|---|---|---|---|
| 6,690,016 | B1 | 2/2004 | Watkins et al. |
| 2001/0050772 | A1* | 12/2001 | Meinlschmidt et al. ...... 356/430 |
| 2002/0172410 | A1 | 11/2002 | Shepard |
| 2003/0165178 | A1* | 9/2003 | Borden et al. ................. 374/5 |
| 2005/0117145 | A1 | 6/2005 | Altman et al. |
| 2006/0029121 | A1 | 2/2006 | Boehmisch et al. |
| 2006/0114965 | A1 | 6/2006 | Murphy et al. |
| 2006/0262971 | A1 | 11/2006 | Foes et al. |
| 2008/0075139 | A1* | 3/2008 | El Jarad et al. ................ 374/5 |
| 2011/0085582 | A1 | 4/2011 | Zagar et al. |

FOREIGN PATENT DOCUMENTS

| | | |
|---|---|---|
| CN | 1902474 A | 1/2007 |
| CN | 1940539 A | 4/2007 |
| DE | 10 2007 055 210 A1 | 11/2008 |
| JP | 02-151356 A | 6/1990 |
| JP | 2-278146 A | 11/1990 |
| JP | 05-066209 A | 3/1993 |
| JP | 07-004559 Y2 | 2/1995 |
| JP | 2002-527745 A | 8/2002 |
| JP | 2006-047313 A | 2/2006 |
| JP | 2006-337230 A | 12/2006 |
| JP | 2006-337232 A | 12/2006 |
| SU | 1712852 A1 | 2/1992 |
| WO | WO 2009/065847 A1 | 5/2009 |

OTHER PUBLICATIONS

Corresponding International Search Report with English Translation dated Jun. 1, 2011 (seven (7) pages).

German-language Written Opinion (Form PCT/ISA/237) (seven (7) pages).

A R Hamzah et al., "An Experimental Investigation of Defect Sizing by Transient Thermography", Insight, vol. 38, No. 3, Mar. 1996, pp. 167-170, 173, XP-000857143.

N. P. Avdelidis et al., "Transient Thermography in the Assessment of Defects of Aircraft Composites", NDT&E International, vol. 36, 2003, pp. 433-439, XP004434271.

Chinese Office Action with partial English translation dated Jan. 6, 2014, with Statement of Relevancy (Sixteen (16) pages).

International Preliminary Report on Patentability (PCT/IB/338 & PCT/IB/373) dated Oct. 18, 2012 (two (2) pages).

English translation (Written Opinion (PCT/ISA/237)) previously filed on Oct. 4, 2012 (six (6) pages).

Japanese Office Action dated Apr. 13, 2015 with English translation (13 pages).

Russian Decision to Grant dated Feb. 11, 2015 with partial English-language translation (thirteen (13) pages).

* cited by examiner

THERMOGRAPHIC TEST METHOD AND TESTING DEVICE FOR CARRYING OUT THE TEST METHOD

BACKGROUND OF THE INVENTION

The invention relates to a thermographic test method for the locally resolving detection and identification of defects near the surface in a test object and to a testing device suitable for carrying out the test method.

Semifinished products of electrically conductive material, for example billets, bars, rods, tubes or wires of metallic materials, may serve as starting materials for high-grade end products and often have to meet extremely high quality requirements. The testing for material defects, in particular for defects near the surface such as cracks, voids or other inhomogeneities in the material, forms an important part of the quality control of these products. During this testing, it is generally endeavored to test the surface of the material as completely as possible with high local resolution, which wherever possible is carried out as early as possible in the production chain in order to decide on the basis of the result of the test, depending on the type of defects found, whether the defects are uncritical for the further processing, or at least can be repaired by reworking such as grinding, or whether the material has to be discarded.

Apart from the magnetic methods that are often used for such tests, such as the eddy current technique or the stray flux technique, nowadays thermographic test methods are also used for the locally resolving detection and identification of defects near the surface in test objects.

In a known thermographic test method, an electrically conducting test object, for example a steel billet, after rolling runs through an induction coil that is under high-frequency alternating current and induces a current flow near the surface of the test object. On account of the skin effect, which is dependent on the excitation frequency, the current density in the vicinity of the surface of the test piece is greater here than inside the test object. Microstructural disturbances, such as for example cracks, that lie in the cross section of the induced electrical current flow act as electrical resistances and deflect the current flow, which tries to find the path of least (electrical) resistance in the material of the test piece. This results in higher current densities, and consequently also greater power losses, at the "constrictions" of the current flow in the region of the defects. The power loss occurring in the region of the microstructural disturbances is manifested by heat being generated in such a way that the, locally limited, affected region in the direct vicinity of a microstructural disturbance assumes a higher temperature in comparison with the undisturbed surrounding area. With the aid of a heat-sensitive camera or other suitable recording device that is sensitive to thermal radiation, the presence of defects near the surface can then be detected in a locally resolving manner on the basis of the local temperature values within a region of the surface that is recorded by the recording device. A visual representation of the surface regions recorded is generally also provided, and thermographically determined anomalies can be automatically assessed by a downstream evaluating system.

DE 10 2007 055 210 A1 describes a thermographic test method and a testing device set up for carrying out the test method. The testing device has an induction coil for heating up a surface area of a metallic test object running through the induction coil, for example a steel billet, and one or more infrared cameras, in order to measure the temperature profile of the steel billet running through. The results of the measurement are used for activating a color marking system, in order to mark defects that are found. For the evaluation of the thermographic images (thermal images) recorded by the infrared cameras, the description provides evaluation software, which analyzes a thermal image or the thermal images and identifies temperature differences above a predetermined threshold value and reports them as a defect. The size of the temperature difference above the predetermined threshold value is regarded as an indication of the depth of the defect. The evaluation software can evaluate defects both with regard to their length and with regard to the size of the temperature difference above the threshold value. The evaluation software can remove defects of a length below a minimum defect length from a defect list, so that such defects are no longer found to be defects. If, however, a defect lies below a minimum defect length but the size of the temperature difference lies above the threshold value, which lies above a maximum size of the temperature difference, such a defect is nevertheless reported as a defect. In this way, a defect is identified in dependence on the defect length and the temperature difference with respect to the surrounding area.

A rise in the temperature profile of more than 2 K with respect to the surrounding area is generally regarded as a defect, but the threshold temperature may also be chosen to be lower. A temperature difference with respect to the surrounding area of 5 K or more is clearly identified as a defect.

In practice, the temperature profile to be evaluated is generally superposed by an interference signal of an appreciable amplitude. Possible sources of interference include local fluctuations in the degree of emission of the surface of the test object, reflections from the surrounding area and circumstances that are generally unavoidable in actual test operation, such as foreign bodies on the surface of the test piece. False indications may also be caused by the geometry of the test piece, since for example edges on square profiles often have an increased temperature in comparison with the surrounding area. Typically, the temperature differences occurring at a crack-like defect in comparison with the surrounding surface are of the order of magnitude of 1 K to 10 K. It has been observed that interference amplitudes may well also be of this order of magnitude. Therefore, in spite of all possible measures to reduce the interference amplitude, it cannot be ruled out that interferences are falsely classified as microstructural flaws or defects.

PROBLEM AND SOLUTION

A problem that is addressed by the invention is that of providing a thermographic test method and a thermographic testing device suitable for carrying out the method that offer improved suppression of interference in the evaluation of thermographic signals in comparison with the prior art. In particular, it is intended to improve the selectivity in distinguishing between actual defects and pseudo-defects attributable to other interferences. It is preferably intended to provide testing of the complete surface of elongated objects of electrically conductive material with increased reliability in the detection and identification of defects.

To solve this and other problems, the invention provides a thermographic test method for the locally resolving detection and identification of defects near the surface in a test object, comprising the following steps: (a) heating up a portion of the test object in such a way that a thermal disequilibrium occurs between defective regions, affected by defects, and material of the test object that is free from defects, a defect-free surrounding area of a defective region not being heated up or heated up less intensely than the defective region; (b) recording a series of thermographic images following one after the other at a time interval within a heat propagation phase, which begins when a heat flow from the locally heated-up defective region into the surrounding area of the defective region manifests itself, each thermographic image representing a local temperature distribution in a surface region of the test object that is recorded by the thermographic image; (c) determining positionally correctly assigned temperature profiles from the thermographic images, a temperature profile being a locally resolving profile, wherein different locations within the temperature profile are respectively assigned values of a measured variable that represents the temperature at the respective location, and each positionally correctly assigned temperature profile being assigned to the same measuring region of the surface of the test object; (d) determining variations over time of temperature values from the temperature profiles for a large number of measuring positions of the measuring region that are recorded by the temperature profiles; and (e) evaluating the variations over time on the basis of at least one evaluation criterion characterizing the heat flow in the measuring region. The invention also provides a thermographic testing device set up for carrying out the method for the locally resolving detection and identification of defects near the surface in a test object, comprising: a heating device for heating up a portion of the test object in such a way that a thermal disequilibrium occurs between defective regions, affected by defects, and material of the test object that is free from defects, a defect-free surrounding area of a defective region not being heated up or heated up less intensely than the defective region; at least one recording device for recording a series of at least two thermographic images one after the other at a time interval; and an evaluating device for evaluating thermographic data of the thermographic images, the testing device being configured for carrying out the thermographic test. Advantageous developments are specified and claimed herein.

In the test method, a portion to be tested of the test object is exposed to the effects of a heating device. Hereafter, this is also referred to for short as "heating up". The heating energy is in this case introduced in such a way that a thermal disequilibrium occurs between defective regions, affected by defects, or flawed locations and the material of the test piece that is free from defects. A flawed location or a defective region in this case includes the actual flaw, for example a crack, and the directly adjacent surrounding area. The defect-free surrounding area may possibly maintain its temperature under the effect of the heating device, that is to say not be heated up, or it may be heated up less intensely than the flawed locations.

In the case of electrically conductive test objects, such as for example metallic billets, bars, wires or the like, an inductive method may be used for example for the heating-up process. The input of thermal energy into the defective regions of the test object may also take place with the aid of ultrasound.

Within a heat propagation phase, a series of two or more thermographic images is recorded, these being recorded at time intervals from one another. The heat propagation phase begins when the heat flow from the locally heated-up defective region into the surrounding area manifests itself. The heat propagation phase extends into the cooling-down phase following the heating-up process and in many cases corresponds to the cooling-down phase. However, there is often no strict limit between the heating-up phase and the cooling-down phase. The beginning of the heat propagation phase may still overlap in time with the phase of the local heating up, since thermal energy can already propagate during the heating-up process.

Each of the thermographic images in this case represents a local temperature distribution in a surface region of the test object recorded by the thermographic image at different points in time during the heat propagation. If the recording device provided for recording the thermographic images, for example a thermal-imaging camera, and the test object are at rest, the surface regions of the test object recorded at different points in time may be identical. If there is a relative movement between the test object and the recording device, the surface regions may be spatially offset in relation to one another.

Positionally correctly assigned temperature profiles are determined from the thermographic images of a series, each of the temperature profiles that are assigned to one another positionally correctly being assigned to the same measuring region of the surface of the test object. The term "measuring region" refers here to a one-dimensionally or two-dimensionally extended region that has a fixed position in the system of coordinates of the test object. Many measuring positions lie in the measuring region.

The term "temperature profile" refers to a locally resolving profile in which different locations or positions within the temperature profile are respectively assigned values of a measured variable that represent the temperature at the respective location. The temperature profile may be understood as a location function, which describes the dependence of the temperature value on the location within the temperature profile. A temperature profile may, in the manner of a line profile, relate to a more or less narrow, almost linear region. It may also concern a 2D profile or area profile, the local distribution of temperature values in a piece of area of a predetermined shape and size then being described by the temperature profile. The measured variable assigned to the different locations of the temperature profile may be referred to as the "temperature value". This does not generally involve measuring the temperature directly, but for example measuring the intensity or amplitude of the thermal radiation emitted by the respective location, which can be converted into a local temperature of a profile location by the means that are customary in thermography.

In this way, a number of temperature profiles (at least two) are determined, representing the local variation in temperature within the same measuring region at different points in time during the cooling-down process. The variations over time of temperature values are then quantitatively determined from the temperature profiles for a large number of measuring positions of the measuring region that are recorded by the temperature profiles, so that the development over time of the local temperature values is obtained for a large number of measuring positions of the measuring region. The variations over time are then evaluated on the basis of at least one evaluation criterion that is suitable for characterizing the heat flow in the measuring region.

In the method, not only are the temperature profiles analyzed with regard to the local variation in temperature represented by them, but also their change over time. A sequence or a series of temperature profiles is obtained for a defined measuring region at the surface and a defined time range. An essential aspect of the method is the inclusion of the heat flow, that is to say the dynamic behavior of the development over time of the temperature profile and the evaluation or interpretation thereof.

Another formulation consequently proposes the use of a variant of the locally resolving heat flow thermography for the detection and identification of defects near the surface in suitable test objects, the development over time of the local distribution of the temperature that can be found at the surface of the test piece being determined and evaluated. This involves, inter alia, quantitatively recording and evaluating the lateral heat flow.

In comparison with the prior art, a much more reliable classification of defects, for example as a crack or a microstructural disturbance, is obtained, since the method allows an improved capability of distinguishing between temperature effects that are attributable to defects and effects that are not caused by heat flow. Furthermore, an improved capability of evaluating the thermographic information is obtained, even in the case of low signal amplitudes, since it is not just the amplitude or the intensity of the temperature signals in the profiles that is decisive but also how they dynamically behave on the time axis. This also results in considerably improved interference suppression even when the interference amplitude (not attributable to the defects sought) is higher than the useful signal amplitude, the useful signal amplitude referring here to the signal amplitude caused by microstructural disturbances.

The test method particularly allows the spatial-temporal heat propagation after a sudden, locally limited influx of heat to be recorded and quantitatively evaluated. In simple terms, the spatial-temporal heat propagation takes place in such a way that the heat concentrated in the region of a potential defect flows away over time into neighboring, cooler regions of the material of the test object. The flowing away is manifested by a lateral surface temperature distribution insofar as a temperature profile at the point of excitation decreases in amplitude over time, but there is a noticeable increase in temperature in the direct vicinity of the excitation position. It follows from this that, under these conditions, the shape of the temperature profiles changes over time in a characteristic manner. The most frequent interfering influences, for example surface reflections, on the other hand, do not undergo any change, or only a small change, over time with respect to their local properties and/or show a change over time that deviates distinctly from the typical heat flow behavior (for example brief flashing of a reflection). Such interfering influences can therefore be clearly distinguished from actual defects on the basis of their typical spatial-temporal behavior. Some interfering influences are indeed manifested in the temperature profile by dynamic spatial-temporal behavior, but this generally differs distinctly from the spatial-temporal heat propagation that takes place in the surrounding area of a defect within a heat-conductive material undisturbed by interference. Therefore, an evaluation which analyzes the spatial-temporal behavior of temperature profiles from the aspects of the laws of heat propagation or heat diffusion in a solid body offers much improved selectivity and interference suppression in comparison with conventional methods.

The evaluation can therefore also be described as comprising in the evaluation a comparison of the recorded thermographic data with a signature, the signature being a description of the spatial and temporal heat propagation in a solid body that endeavors, especially after a local concentration of heat, to re-establish the thermal equilibrium.

In a preparatory evaluation step, the temperature profiles are preferably automatically analyzed for whether defect-like anomalies are evident in the temperature profile, that is to say anomalies that could be attributed to a defect, but not necessarily. In the identification of defect-like anomalies, preferably a local maximum of the temperature values within the temperature profiles is sought. The local maximum corresponds here to a location within a temperature profile of which the temperature is distinctly higher than the temperature at profile locations in the directly surrounding area of the local maximum. The identification step is intended, for example in crack testing, to find substantially narrow hot locations in an otherwise cooler surrounding area. In this identification step, suitable image-processing filter routines may be used, in order for example to distinguish a local maximum from edge locations at which the temperature increases or decreases abruptly or in a step-like manner, as it were, over a short distance from one side of the surrounding area to the other side of the surrounding area. Generally, two or more filter routines operating on the basis of different criteria are used for this purpose, in order to identify those image locations (pixels or pixel groups) that are clearly attributable to a local temperature maximum.

The evaluation can then concentrate on those regions in which local temperature maxima have been found. In a method variant, the variation over time of the amplitude of a temperature value in the region of a local maximum of the temperature values of a temperature profile is evaluated as the evaluation criterion. This can be used for example to determine the cooling-down rates in the region of the local maximum and in the vicinity thereof. It has been found that cooling-down rates in the region of microstructural disturbances, such as cracks, within an otherwise undisturbed surrounding area can be well described by laws of heat diffusion and, as a result, can be used as a reliable assessment criterion. Cracks and other defects can therefore often be distinguished from disturbances not attributable to defects just on the basis of the typical cooling-down rates.

Alternatively or in addition, in the evaluation a heat volume concentration value in the region of a local maximum of the temperature values within a temperature profile may be determined and the variation over time of the heat volume concentration value evaluated. The heat volume concentration value is a measure of how the volume of heat of the local maximum relates in comparison with the directly surrounding area. If this heat volume concentration falls over time, heat flows away into the surrounding area, as is typical for example in the surrounding area of cracks. If, on the other hand, the local maximum is not attributable to a microstructural disturbance or a crack, the heat concentration value often shows significantly different behavior, it even being possible for example for the heat concentration to continue initially to increase after the heating-up process has been ended. This is then an indication that the local temperature maximum is not attributable to a crack or the like.

In order to be able to determine with sufficient accuracy appropriate time functions for the evaluation of the variations over time by way of calculated characteristic variables, in preferred embodiments at least three temperature profiles recorded one after the other in time are evaluated together, in order to obtain a suitable number of interpolation points. Generally between four and ten temperature profiles are evaluated together, so that there are an adequate number of interpolation points in the time domain and a reliable distinction can be made between defects and artefacts.

Alternatively or in addition to the determination and evaluation of characteristic variables from time functions, it is also possible to perform the variations over time of temperature values within the temperature profiles on the basis of image elements (pixels) or groups of image elements (pixel groups). The results are then brought into relation to one another in order to arrive at spatial-temporal signatures. Generally, every variant of signal evaluation that allows dimensional figures or data for a comparison of the signal properties with the theoretical principles of heat propagation in a solid body can be applied. For example, spatial-temporal line profiles, recording sequences, pieces of areas, any desired pixel arrangements or pixel patterns may be used. What is essential is joint consideration or inclusion of the spatial and temporal aspects, without which it would scarcely be possible to make a reliable statement as to defect probabilities.

It is possible to use the test method in testing devices in which both the test object and the recording device for recording thermographic images are at rest. This simplifies the positionally correct assignment of the temperature profiles to one another considerably, since the same measuring region in thermographic images recorded one after the other in time respectively corresponds to the same image region (same image coordinates) in the thermographic images.

In preferred applications, however, the test method is used for testing elongated test objects, such as for example bars, tubes, wire or the like. For testing elongated test objects, a relative movement may be produced between the test object and a recording device for recording the thermographic images parallel to a direction of movement, which expediently extends parallel to the longitudinal direction of the elongated test object. In this case, the recording device is preferably at rest, while the test object is moved in relation to the recording device. The relative movement is produced in such a way that the surface regions that have respectively been recorded by the thermographic images recorded one after the other in time are arranged offset by a specific distance parallel to the direction of movement. The surface regions recorded directly one after the other in time in this case preferably overlap partially in such a way that each location of the surface under test is recorded by two or more thermographic images. As a result, testing of the complete surface of elongated test objects moving in the longitudinal direction is possible. Preferably, each location of the surface of the test piece occurs in three or more thermographic images, for example in four to twenty or more thermographic images, the location lying at a different point (image position) in each of the thermographic images on account of the relative movement.

The positionally correct assignment of temperature profiles of different thermographic images represents a particular challenge in the testing of moving test objects. In a variant of the method, a first thermographic image, recorded at a first point in time, of a series of thermographic images is analyzed by image processing, in order to identify at least a first selected image detail that contains thermographic data of a first surface detail with a defect-like anomaly. The identical surface detail is then automatically found in a second image detail corresponding to the first image detail. The second image detail is located in a second thermographic image, recorded at a time interval from the first thermographic image at a later, second point in time. Then a joint evaluation of the thermographic data of the first and second image details takes place, in order to achieve the positionally correct assignment.

For automatic finding, an expected position of the surface detail containing the defect-like anomaly in the second thermographic image is preferably determined on the basis of a measured, or in some other way known, relative speed between the test object and the recording device and the time interval that has passed between the first point in time and the second point in time, in order to determine that path that the surface detail has covered in the direction of movement between the first point in time and the second point in time. This allows the evaluation of the second thermographic image to concentrate from the beginning on that surface detail in which a defect-like anomaly was found in the analysis of the first thermographic image, recorded at an earlier time.

For finding the defect-like anomaly, preferably a local maximum of the temperature values is sought within at least one linear or areal temperature profile in the first thermographic image. Suitable image-processing filter routines may be used for this purpose.

The invention also relates to a thermographic testing device set up for carrying out the method, for the spatially resolving detection and identification of defects near the surface in a test object. The testing device comprises:

a heating device for heating up a portion of the test object in such a way that a thermal disequilibrium occurs between defective regions, affected by defects, and material of the test piece that is free from defects;

at least one recording device for recording a series of at least two thermographic images one after the other at a time interval; and an evaluating device for evaluating thermographic data of the thermographic images, the evaluating device being configured for determining positionally correctly assigned temperature profiles from the thermographic images, for determining variations over time of temperature values from the temperature profiles for a large number of measuring positions of the measuring region that are recorded by the temperature profiles, and for evaluating the variations over time on the basis of at least one evaluation criterion characterizing the heat flow in the measuring region.

The recording device is preferably an area-scan camera sensitive to thermal radiation, with a large number of image rows, the image information of which is evaluated together.

These and further features emerge not only from the claims but also from the description and the drawings, where the individual features can be realized in each case by themselves or as a plurality in the form of subcombinations in an embodiment of the invention and in other fields and constitute advantageous and inherently protectable embodiments. Exemplary embodiments are represented in the drawings and are explained in more detail below.

BRIEF DESCRIPTION OF THE DRAWINGS

FIG. 3 shows in 3A a schematic plan view of a heated-up portion of the moving test object lying in the recording region of a thermal-imaging camera, with a selected image detail, which is also shown enlarged and contains a defect, and in 3B an explanation of a method for the positionally correct joint evaluation of temperature profiles recorded at different points in time on the same area of a surface;

FIG. 4 shows respectively in 4A and 4B the development over time of parts of a temperature profile in the region of a local temperature maximum of the temperature, the positionally correctly assigned details of temperature profiles in the region of a disturbance not attributable to a crack being shown in 4A and corresponding temperature profiles in the region of a crack near the surface being shown in FIG. 4B;

FIG. 5 shows respectively in FIGS. 5A and 5B the variations over time of two characteristic variables characterizing the heat flow in the region of the local temperature maximum, the variations over time of the characteristic variables for a disturbance not attributable to a crack being shown in FIG. 5A and the corresponding variations over time for a crack near the surface being represented in FIG. 5B; and FIG. 6 shows in 6A a detail from a temperature profile with a local temperature maximum attributable to a reflection, in FIG. 6B the development over time of the local variation in temperature in the region of the local temperature maximum shown in FIG. 6A and in 6C the development over time of two characteristic variables characterizing the heat flow in the region of the local maximum.

DETAILED DESCRIPTION OF THE PREFERRED EMBODIMENTS

Figure 1:
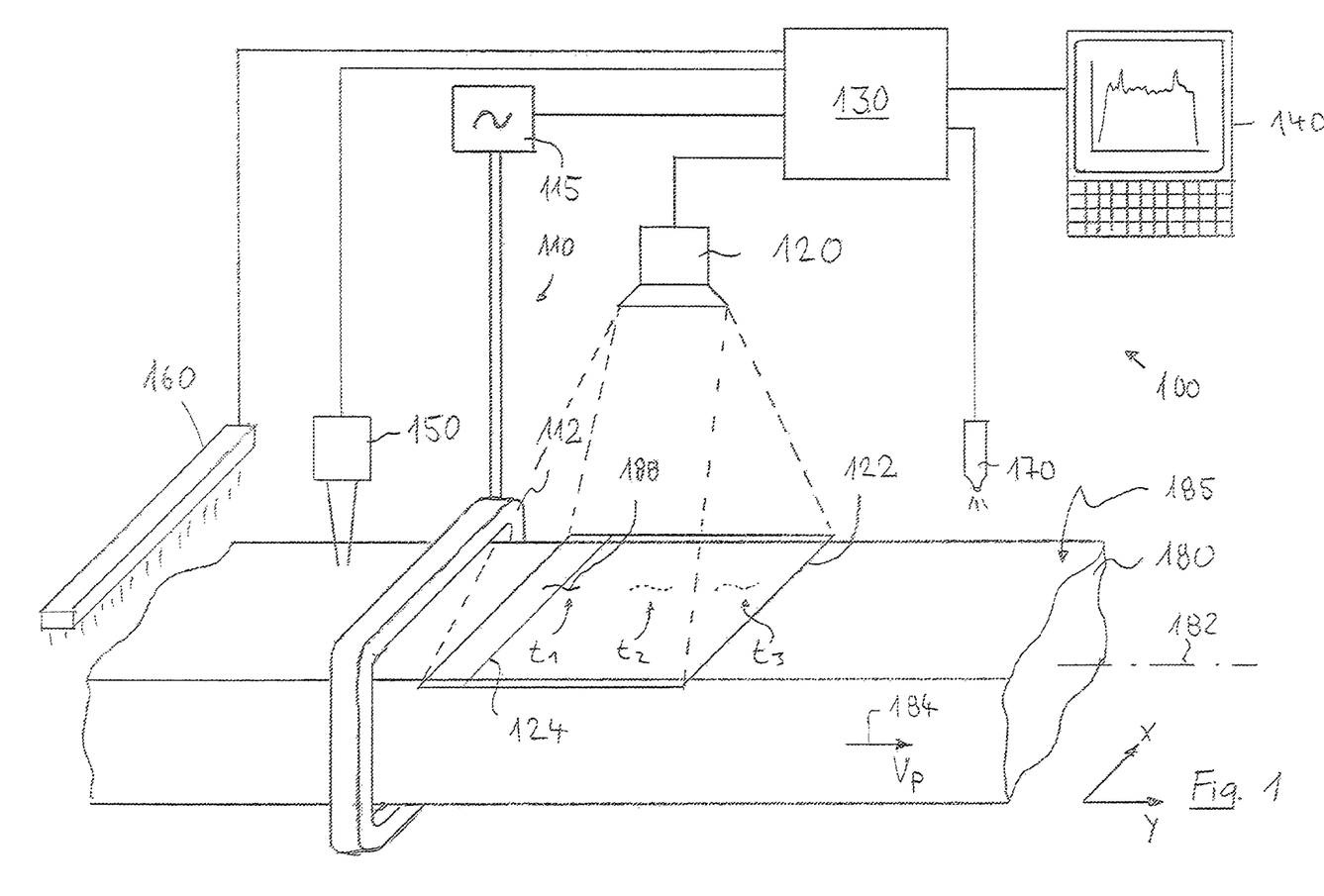
FIG. 1 shows an embodiment of a testing device for the thermographic testing of elongated test objects of electrically conductive material by the run-through method.

FIG. 1 shows a schematic representation of an embodiment of a thermographic testing device 100 for testing the complete surface of elongated test objects of electrically conductive material by the run-through method. In the case of the example, the test object 180 is a steel billet with a rectangular cross section, which comes from a rolling device (not represented) and is conveyed with the aid of a conveying device (not represented), for example a roller conveyor, at a largely constant running-through speed $v_P$ from the range between about 0.1 m/s and 1.5 m/s in a direction of movement 184 (arrow) extending parallel to its longitudinal axis 182. After the hot rolling, the steel billet does not have a bright surface but a so-called "black" surface, the surface temperature of which typically lies between 0° C. and 50° C. The thermographic testing and the evaluation of the thermographic data thereby recorded are explained on the basis of the testing of the macroscopically level surface 185 of the test piece. Corresponding tests are also carried out at the same time for the other three surfaces of the test object.

The testing device has an inductive heating device 110 for heating up a portion of the test object entering the effective region of the heating device, in such a way that a thermal disequilibrium occurs between defective regions, affected by defects, and material of the test object that is free from defects. The heating device includes an induction coil 112, which is designed as a flat run-through coil for the test object, with a coil plane aligned perpendicularly to the running-through direction. The induction coil is electrically connected to an AC voltage generator 115, which for activation is connected to a central control device 130 of the testing device. When the induction coil 112 is excited with AC voltage of a suitable frequency, eddy currents are induced in regions near the surface of the test object and can heat up the regions near the surface to temperatures above ambient temperature when said object runs through the induction coil. The heating-up process is normally relatively uniform in the defect-free regions of the surface. If, however, microstructural disturbances such as cracks, cuts, voids or the like occur in the cross section of the induced current flow, these act as electrical resistances and deflect the current flow. This leads to higher current densities, and consequently to greater power loss, at the constrictions of the current flow. This power loss at the microstructural disturbances is manifested by additional generation of heat, so that the, locally limited, affected region of the defect in the direct vicinity of the microstructural disturbance has a higher temperature in comparison with the undisturbed surrounding area. There is therefore a local heating up with respect to the lower temperature level of the surrounding area further away. Typical temperature differences between the region of a crack and the directly adjacent undisturbed surrounding area of the material are often of the order of magnitude of between about 1 K and 10 K. These local temperature increases and their spatial-temporal development are used in the test method for the locally resolving detection and identification of defects near the surface.

In the case of the example, the generator has an electrical power output of up to 150 kW and AC voltage frequencies from the range between 10 kHz and 350 kHz are used. Heating devices with other specifications are likewise possible. For example, the AC voltage generator may be operated with power outputs of up to several MW, which may be advantageous for example in the case of test objects with greater dimensions (for example a diameter of more than 800 mm). The frequency range may be adapted to the measuring task. For example, frequencies of up to 1 MHz may be useful in order to find particularly small defects near the surface, since the depth of penetration of the eddy current becomes less with increasing frequency, and consequently the measurement volume decreases. Higher frequencies are also of advantage when testing electrically conducting steels with high electrical resistance and magnetic permeability close to 1, in order to achieve rapid local heating up of defective regions with respect to their surrounding area.

The heating device brings the overall system comprising the test object/defect into a thermal disequilibrium. With the aid of the test method and the testing device, it is possible to observe both in the location domain and in the time domain the way in which the system resists the state of thermal equilibrium.

For this purpose, the testing device has a locally resolving recording device 120 that is sensitive to thermal radiation, for recording two-dimensional thermographic images, which can be recorded at a high image frequency of up to 100 images per second (frames per second). The recording device, also referred to hereafter as a "heat-sensitive camera", is connected to the central control device 130 for controlling the image recording and for taking over and evaluating the thermographic data obtained in the thermographic images. Integrated in this control device is a computer-based image-processing system, which is set up for the purpose of evaluating the thermographic data determined from the thermographic images on the basis of different criteria. Such a heat-sensitive camera may provide a visual representation of the presence, and some of the properties, of microstructural disturbances, on the basis of local temperature values or on the basis of locally determined thermal radiation, and it can automatically assess these anomalies with the aid of suitable image-processing means in an associated evaluating system.

The heat-sensitive camera 120 is an area-scan camera and has a rectangular recording region 122, which is also referred to here as the image field 122 and in the case of the example covers the entire width of the surface 185 of the test piece facing it, beyond the lateral edges. In the case of the example, the heat-sensitive camera 120 covers an image field 122 of the size 270 mm×216 mm with a resolution of 640×512 pixels (image elements). An image element (pixel) in this case corresponds to a relatively small rectangular surface detail of 0.5 mm to 0.8 mm in diameter on the surface 185 of the test piece. A thermographic image recorded with the area-scan camera consists of a large number of lines extending substantially perpendicularly to the longitudinal direction of the test object (y direction) and columns extending substantially parallel to the longitudinal direction (i.e. in the y direction). The thermographic images are evaluated row by row, in order to reliably detect longitudinal flaws in particular. A narrow measuring region 124 of a linear nature associated with a row of the heat-sensitive camera extends transversely in relation to a defect 188. This measuring region is aptly also referred to as a measuring line.

At the point in time $t_1$ represented in FIG. 1, the defect 188 near the surface is in the form of a longitudinal crack, extending more or less parallel to the longitudinal direction of the test object, in the vicinity of the entry side of the recording region facing the induction coil 112. The positions of the same longitudinal crack at later points in time $t_2>t_1$ and $t_3>t_2$ are represented by dashed lines in order to illustrate that one and the same defect or one and the same surface detail can be located in the recording region 122 of the heat-sensitive camera at different points in time, but the image positions within the thermographic image are offset with respect to one another respectively in the direction of movement 184 by a specific distance in the direction of movement 184 in dependence on the running-through speed $v_P$ and the time interval between the recording times of the thermographic images following one after the other at a time interval.

The image recording frequency used for the heat-sensitive camera is adapted to the running-through speed of the test object in such a way that each surface portion of the surface 185 of the test piece occurs at different points in a number of thermographic images, for example in at least 5 or at least 10 or at least 15 thermographic images recorded at time intervals from one another.

An indicating and operating unit 140 connected to the control device has a screen, on which data and relationships determined from the thermographic images can be displayed. With the aid of a keyboard and/or other input means, the testing device can be conveniently set up for various testing tasks and operated by an operator.

Also connected to the control device 130 is a speed-measuring device 150 for determining the speed of movement $v_P$ of the test object at a given time. In the case of the example, this device, serving as a position encoder, operates contactlessly with the aid of laser radiation. In other embodiments, a tactile position encoder may be provided, for example with a measuring wheel rolling on the surface of a test piece.

The precision of the thermographic test method may be greatly influenced by fluctuations in the degree of emission of the thermographically recorded surface of the test piece. In order to minimize as far as possible resultant negative influences, an active homogenization of the degree of emission of the measured surface of the test piece is performed, in that the surface of the test piece is wetted uniformly with a liquid, for example water, with a wetting device 160 before passing through the induction coil. This technique has proven to be effective at surface temperatures of up to 50° C. for largely avoiding the occurrence of pseudo-indications attributable to local fluctuations of the degree of emission.

If an anomaly is clearly identified as a defect by the testing device, it can be marked with the aid of an automatic marking device 170 connected to the control device 130, by spraying on dye or the like, so that a possible reworking of the disturbed surface of the test piece or a segregation of badly disturbed portions in a purposeful manner is possible.

There follows a description of a preferred variant of a test method that can be carried out with the aid of the testing device for the locally resolving detection and identification of defects near the surface in test objects running through the testing device at a high running-through speed. Regions of the test object that are near the surface are inductively heated up by the induction coil 112, local temperature maxima occurring in the region of cracks and other microstructural disturbances. After the corresponding portions of the test object have passed through the induction coil, these regions cool down again. The recording device 120 is provided directly after the induction coil in the direction of movement and records the surface regions in this cooling-down phase.

Figure 2:
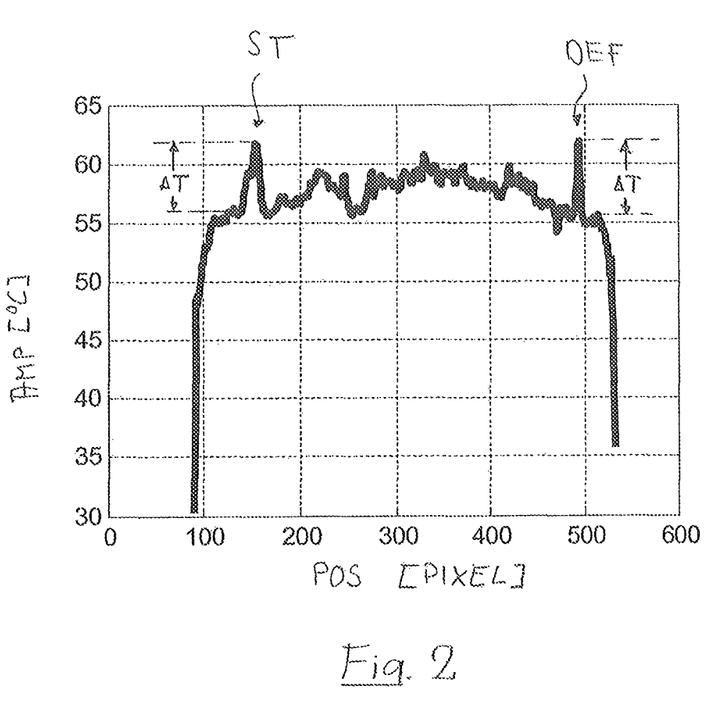
FIG. 2 shows an example of a temperature profile recorded perpendicularly to the direction of movement of the test object.

In a first method step, thermal anomalies in the part of the surface of the test piece that is moved into the recording region 122 are identified. For this purpose, corresponding rows, assigned to the entry side, are evaluated, in order for example to obtain a locally resolving temperature profile (line profile) perpendicularly to the running-through direction along a measuring line 124. FIG. 2 shows such a temperature profile by way of example. The position POS of measuring locations within a linear measuring region extending perpendicularly to the direction of movement (y direction) in the x direction is indicated on the x axis by indicating numbers of the corresponding pixels (image elements) of a row of the image field. The y axis represents the amplitude AMP of the thermal radiation assigned to the locations and in the case of the example is represented as the absolute surface temperature in degrees Celsius. It is evident that the surface temperature between the lateral edges (approximately at pixel numbers 90 and 540) lies in the range between 55° C. and 60° C. and varies locally by a few K. The temperature profile contains two anomalies, namely a first local temperature maximum ST approximately at pixel no. 150 and a second local temperature maximum DEF approximately at pixel no. 495. In the case of both local temperature maxima, the difference in temperature $\Delta T$ with respect to the directly surrounding area is approximately 6 to 7 K. An evaluation, explained in more detail later, shows that the first local temperature maximum ST is due to an interference that is not attributable to a crack or other microstructural disturbance, while the second temperature maximum DEF was actually caused by a crack near the surface. It is evident that the size of the temperature difference $\Delta T$ alone is not a reliable criterion for distinguishing between actual microstructural disturbances and other anomalies that are not attributable to microstructural disturbances.

Figure 3A:
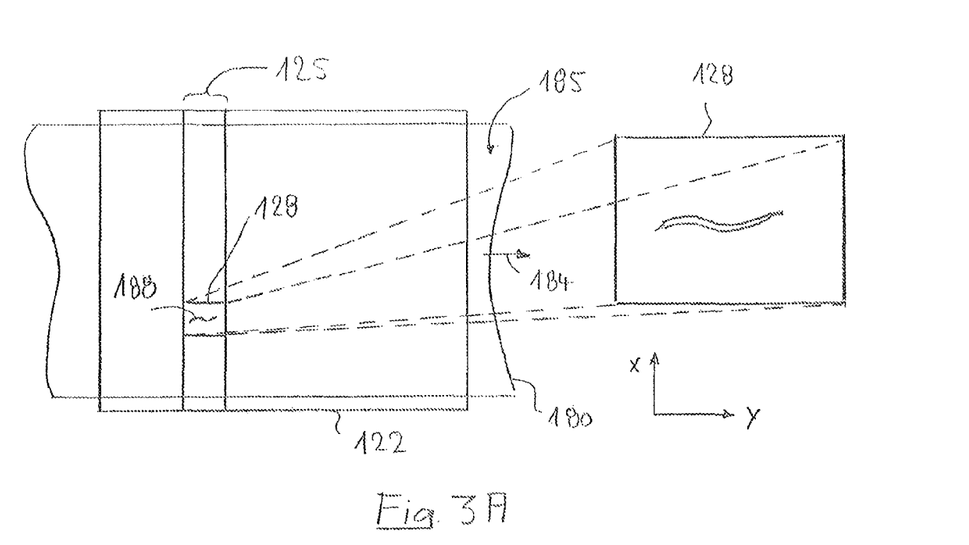

Each thermographic image contains a large number of such temperature profiles locally resolving in the x direction. The occurrence of local temperature maxima is automatically recorded by the image-processing evaluation software, suitable filter routines being used in order to compare the temperature values of pixels or pixel groups within a temperature profile with temperature values of neighboring pixels or pixel groups and, on the basis of the comparison, clearly identify local temperature maxima as such and distinguish them from other artefacts, for example the rapid drop in temperature at an edge. In the filtering, the evaluation software operates row by row within strips extending transversely to the direction of movement, which respectively comprise a large number of neighboring temperature profiles. FIG. 3 shows such a strip 125, which contains the defect 188. The probability of the presence of a crack-like defect in the longitudinal direction increases in this evaluation if, with a large number of neighboring temperature profiles within the strip, a local temperature maximum of a noticeable height occurs at approximately the same pixel position.

The test method is not only based on the evaluation of spatial temperature profiles, that is to say such temperature profiles that represent the local temperature distribution, but also on the analysis of their change over time. This combination is also referred to here as a spatial-temporal analysis. For this purpose, it is not sufficient to analyze a single temperature profile, but instead a number of temperature profiles recorded at a time interval from one another are set positionally correctly in relation to one another for the same measuring region of the surface, in order to be able to analyze the dynamic spatial-temporal behavior of the development of the temperature distribution.

In the embodiment of the test method that is described here, a special variant of pattern detection is used in order to relocate positionally correctly an anomaly identified in a thermographic image from an earlier time that could represent a defect in thermographic images recorded later, and thereby create the possibility of obtaining a time sequence of a large number of temperature profiles from the same measuring region in spite of movement of the test object in relation to the heat-sensitive camera. For this purpose, a strip 125, associated with a specific surface detail, of a first thermographic image at an early time is evaluated row by row and analyzed for the presence of anomalies, in particular local temperature maxima. On the basis of the temperature data of the individual rows, a contiguous area is calculated, enclosing the region of the local temperature maxima constituting the anomaly. A selected rectangular image detail 128, enclosing the defect 188, is shown on the left in FIG. 3 within the strip 125 and on the right in an enlarged representation. The local coordinates of the selected image detail 128, i.e. its position within the thermographic image, represent the position of the associated surface portion of the test object containing the defect 188 at the recording time of the first thermographic image. The image information contained in the selected image detail comprising the spatially contiguous pixels can be treated in the image-processing software as a Binary Large Object (BLOB) and represents a certain pattern of data that can be re-located in thermographic images recorded later.

On the basis of the "pattern", represented by the data structure, of the region around the defect 188, the same pattern is then sought in a number of later thermographic images, recorded afterwards at time intervals, in order to find those image details that correspond as positionally accurately as possible to that surface detail that was used in the analysis of the first thermographic image for the calculation of the pattern sought. Preferably, the image details corresponding to a specific surface detail are sought in at least 5 to 10 thermographic images recorded one after the other and the image information thereof is then evaluated together.

In order to limit spatially the region covered by the search in thermographic images recorded later, and thereby speed up the evaluation, an expected position of the surface detail containing the defect-like anomaly in the thermographic images recorded later is determined on the basis of the speed of movement $v_P$ of the test object, measured with the aid of the speed measuring system 150, the direction of movement 184 and the time interval that has passed between the individual recording times of the thermographic images, in order to calculate respectively from this in each case the distance that the surface detail of interest has covered between the time of the first analysis and the recording time of the thermographic image respectively obtained later. It has been found that, even with a slightly fluctuating running-through speed, the surface portion of interest, or the data associated with this portion, is in this way re-found with an accuracy in the range of the measuring accuracy of the position encoder (here for example about ±1 mm), which in the case of the example corresponds to a locational accuracy of the order of magnitude of about ±2 pixels on the surface of the test piece. Final corrections for positionally correct superposing are then performed computationally, by means of software, by the tracking, i.e. by the pattern recognition, whereby an effective positional accuracy of about ±1 pixel or ±0.5 mm is achieved on the surface of the test piece.

This procedure takes into account the fact that, in practice, the test conditions are usually not ideal. For example, as a result of slippage between the test material and the conveying system, bending of the test material and/or slowing of the test material when it is being loaded onto a roll and subsequent speeding up may bring about fluctuations in the speed and other causes of positional inaccuracies. Resultant problems for testing are avoided by the combination of speed measurement, the finding of surface portions potentially affected by defects on the basis of this measurement and the subsequent search for surface patterns (tracking).

Figure 3B:
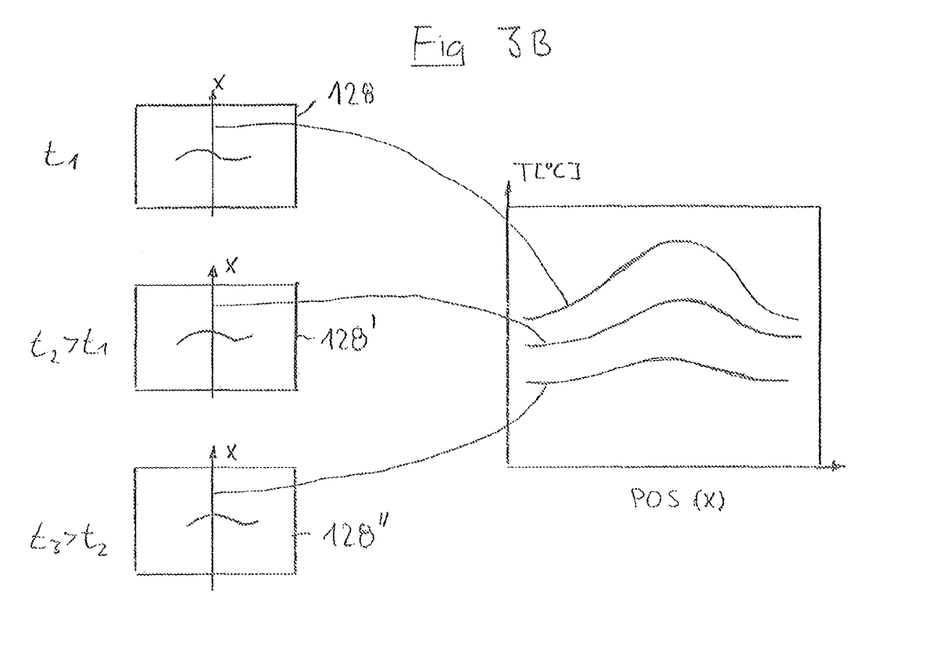

In each of the image details recorded one after the other in time, one or more temperature profiles extending over the location of the potential defect can then be determined and evaluated together. If, as shown in FIG. 3B, the locations of the temperature profiles are respectively located at the same point within the selected image portion, each of the positionally correctly assigned temperature profiles corresponds to the same line-like measuring region of the surface of the test object, this measuring region extending over the position of the potential defect. To explain this, three image details 128, 128' and 128" associated with the same surface detail and recorded at different points in time $t_1$, $t_2 > t_1$ and $t_3 > t_2$ are shown on the left in FIG. 3B, a temperature profile that extends over the defect in the x direction being determined in each of the image details. In the part of the figure on the right, the temperature profiles recorded one after the other in time are presented together, the x axis indicating the position POS (x) in the x direction and the y axis indicating the temperature T. In this way it is possible to determine the spatial-temporal heat propagation in the region of a potential defect highly accurately on a moving test object.

Each of the temperature profiles represents a region extending transversely in relation to the defect, in which the defect lies approximately in the middle. Each of the temperature profiles has a local temperature maximum, the level of which with respect to the surrounding area decreases as time passes (quantified for example by the temperature difference ΔT), whereas the width of the maximum, given for example by the full width at half maximum, in the location domain increases as time passes. These positionally correctly assigned local temperature profiles, recorded one after the other in time, then allow quantitative conclusions to be drawn with respect to the spatial-temporal heat propagation in the region of a potential defect and can be evaluated as follows.

Figure 4A:
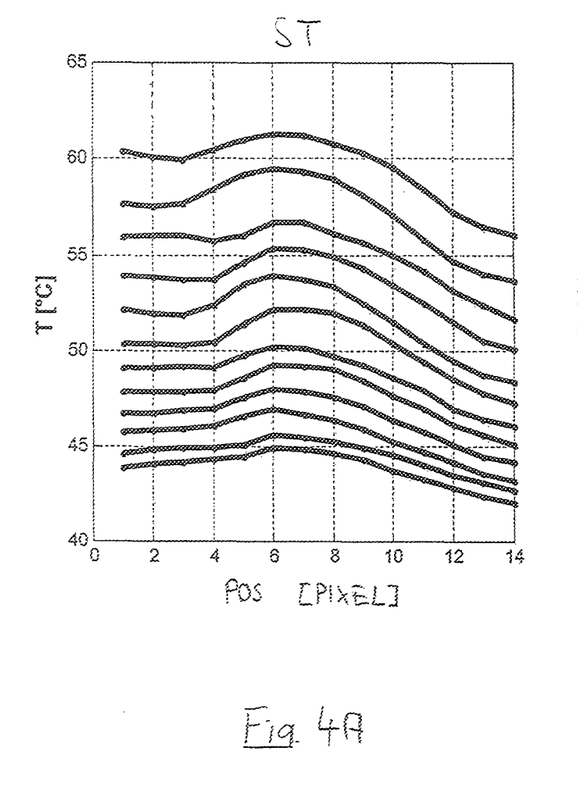
Figure 4B:
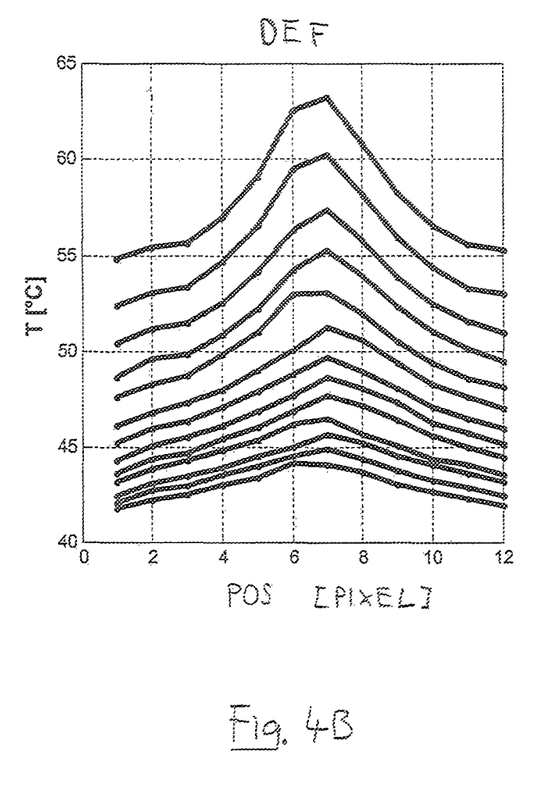

FIG. 4 shows respectively in 4A and 4B representations of a large number of positionally correctly assigned temperature profiles together, the temperature profiles that are respectively shown at the top in the representations having been recorded at earlier times than the temperature profiles respectively shown below them. FIG. 4A shows typical temperature profiles for a disturbance ST, which though it produces a local temperature maximum at approximately pixel no. 7, is not attributable to a crack near the surface. FIG. 4B shows for comparison the positionally correctly assigned temperature profiles from the region of a crack-like defect DEF, here too the local temperature maximum respectively lying in the region of pixel no. 7. The positionally correctly assigned temperature profiles are then analyzed on the basis of evaluation criteria, which on account of the spatial-temporal development of the temperature profiles allow relatively reliable conclusions to be drawn as to whether the spatial-temporal development of the temperature distribution corresponds to the expected dynamic behavior, caused by the heat flow, in the region of a crack or other microstructural disturbance, or conforms to other laws.

Figure 5A:
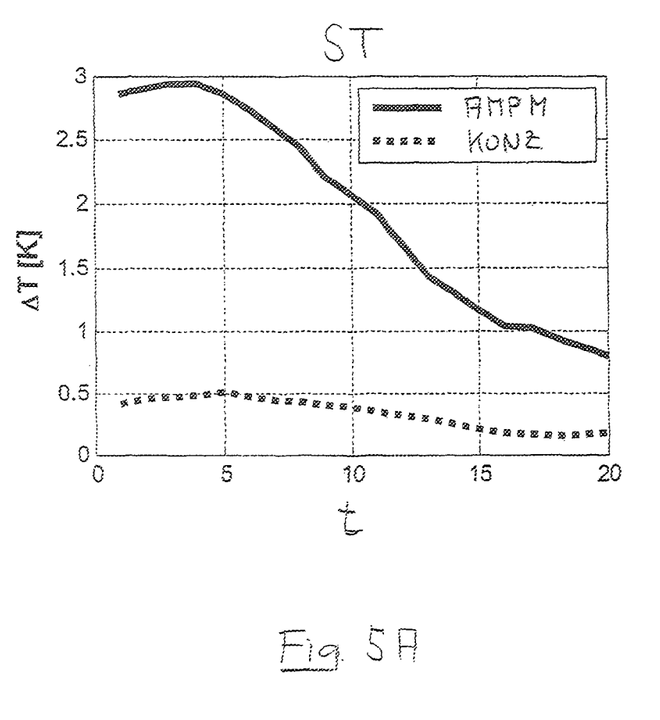
Figure 5B:
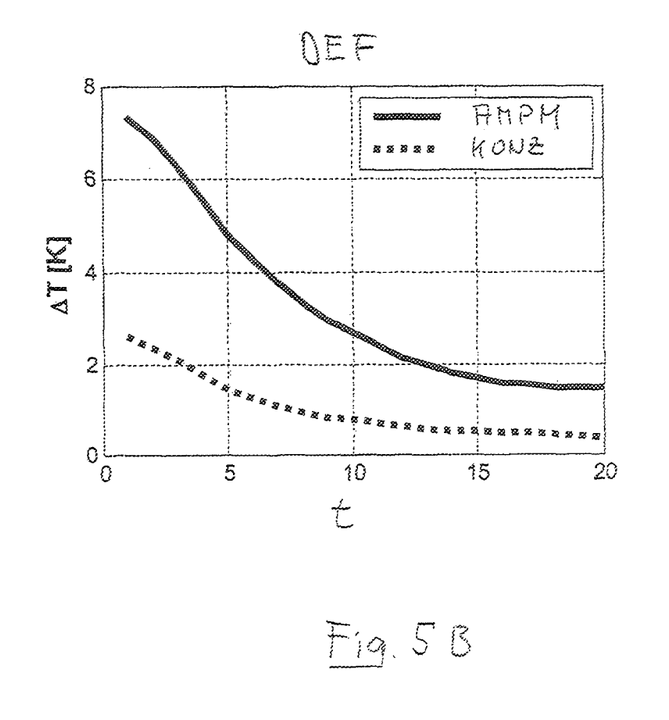

One of the evaluation criteria or characteristic variables is the amplitude AMPM of the temperature value at the location of the local temperature maximum within a temperature profile. Another characteristic variable that has proven to be very reliable for assessing the dynamic behavior of the heat propagation is the heat concentration value KONZ in the region of a local maximum of the temperature values within the temperature profiles. FIG. 5 shows in 5A the variation over time of the amplitude AMPM and of the concentration value KONZ at various time increments t for a disturbance ST not attributable to a crack and in FIG. 5B the variation over time of the same characteristic variables in the same time window for a crack DEF near the surface. The temperature difference ΔT of the temperature at the location of the local maximum with respect to the surrounding area is respectively indicated on the y axes.

It has been found in a large number of tests that, in the region of cracks, both the cooling-down rate, or the change over time in the temperature at the location of the local temperature maximum, and the loss in concentration are relatively great and differ significantly from the corresponding values that can be demonstrated in the region of disturbances that are not attributable to cracks or other microstructural disturbances. With the temperature maximum, which is represented by the amplitude AMPM, the temperature at the location of the local maximum, it has been found that it decreases continuously after completion of the heating-up phase, i.e. during the cooling-down process, and does so with a relatively high cooling-down rate. In the case of the example, a high probability of the presence of a crack is assumed if the cooling-down rate in the region of at least five thermographic images recorded one after the other is greater than a predetermined threshold value for the cooling-down rate. The heat volume concentration value KONZ is a measure of the ratio of the volume of heat directly at the local temperature maximum in comparison with the nearby surrounding area. If the heat concentration value falls over time, this is an indication that heat is, inter alia, flowing away laterally into the surrounding area. This is the case for example with cracks and is accordingly considered to be a sign that the observed signal was caused by the heat propagation in the solid body in the vicinity of a crack.

In the case of the example of a disturbance not attributable to a crack that is explained on the basis of FIG. 5A, on the other hand, the heat volume concentration KONZ is lower from the outset than in the case of a crack; furthermore, the heat volume concentration value initially increases at the beginning of the observed time interval, before it gradually falls. The maximum amplitude AMPM also initially increases, before it falls with a relatively low cooling-down rate, which is distinctly less than the cooling-down rate expected in the region of a crack (FIG. 5B).

Other deviations of the spatial-temporal behavior of the heat volume concentration from the typical behavior caused by heat flow in the case of defects may also occur and be used as an indication of a disturbance that is not attributable to a crack or the like. For example, the heat volume concentration value may remain largely constant over a relatively long time or appear to increase or decrease disproportionately.

These examples show that the analysis and quantitative evaluation of spatial-temporal developments of temperature profiles make it possible to distinguish reliably between different causes of local temperature maxima first found in a temperature profile. If, in the case of an anomaly that is first found, the characteristics described in conjunction with FIGS. 4B and 5B are in principle established, the cause is classified as a crack and, if appropriate, the corresponding surface portion is marked by the marking device 170. If, on the other hand, the spatial-temporal analysis shows a behavior that is untypical of cracks, voids and other microstructural disturbances (cf., for example, FIGS. 4A and 5A), a crack is not indicated. In this way, pseudo-indications can be avoided with a high degree of reliability. The inclusion of the spatial-temporal heat propagation in the region of a potential defect contributes decisively to the interference suppression in the detection and identification of defects with the aid of thermographic signals.

Figure 6A:
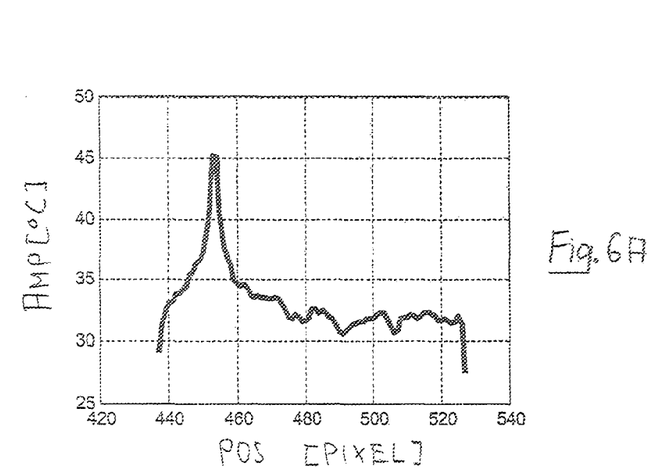
Figure 6B:
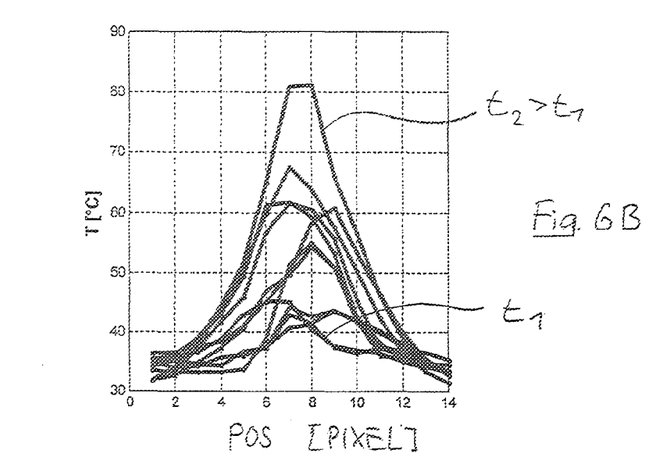
Figure 6C:
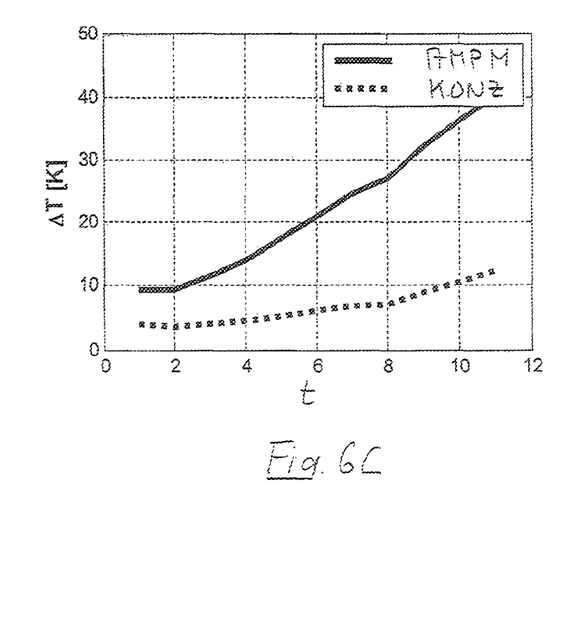

On the basis of FIG. 6, it is explained once again by way of example in what way the analysis of the spatial-temporal heat distribution can contribute to interference suppression. For this purpose, FIG. 6A shows the detail of a temperature profile which, for instance in the region of pixel 455, contains a very pronounced local temperature maximum with a temperature difference ΔT of at least 10 K with respect to the surrounding area. In the case of some conventional testing systems, such indications would be automatically considered to be a sure sign of the presence of a deep crack and the test object would be correspondingly marked and possibly discarded. The spatial-temporal analysis of the heat propagation, however, shows that a crack is not concerned. In FIG. 6B, positionally correctly assigned temperature profiles from the region of the local maximum for different points in time are shown. A special feature in comparison with the profiles from FIG. 4 is that the profile with the greatest amplitude was recorded at a later time ($t_2 > t_1$) than the profile with a distinctly smaller amplitude that was recorded at the earlier point in time $t_1$. The anomaly can also be seen from the variations over time, shown in FIG. 6C, of the characteristic variables of the amplitude of the local maximum (AMPM) and the heat volume concentration value (KONZ). Both values increase with time, which cannot be explained by heat propagation in the region of a locally heated-up crack. In the case of the example, the strong local temperature maximum shown in FIG. 6A is attributable to a reflection at the corresponding location of the surface of the test piece. Since the development over time of the temperature profiles does not show in any respect a propagation behavior that is typical of cracks, such a reflection would therefore not lead to a classification as a crack. On the other hand, it is highly probable that the reflection would be wrongly interpreted as a crack by conventional systems.

Alternatively or in addition to the characteristic variables explained here by way of example, other characteristic variables may also be used as the evaluation criterion. For example, derivatives of the time functions described, for example the changing of the cooling-down rate over time, may be used for this purpose. Since the heat propagation can in essence be described by solutions of the heat diffusion equation, it is also possible to quantify the development over time of the temperature profiles in the region of a local maximum by fitting a Gaussian curve or an error function, a good fit in these cases allowing the assumption that there is a heat propagation dominated by heat flow, while a poor fit suggests other causes. It is also possible to fit polynomials as approximation functions to the temperature profiles and to draw a distinction between the defects sought (for example cracks) and uncritical interferences (for example reflections) by the analysis of polynomial coefficients.

The invention claimed is:

1. A thermographic test method for locally resolving detection and identification of defects near a surface in a test object, the method comprising the acts of:
heating up a portion of the test object such that a thermal disequilibrium occurs between defective regions, affected by defects, and material of the test object that is free from defects, a defect-free surrounding area of a defective region not being heated up or heated up less intensely than the defective region, the surrounding area being located laterally with respect to the surface of the test object;
recording a series of thermographic images one after another at a time interval within a heat propagation phase, which heat propagation phase begins when a lateral heat flow with respect to the surface of the test object from the locally heated-up defective region laterally into a surrounding area of the defective region manifests itself, each thermographic image representing a local temperature distribution in a surface region of the test object that is recorded by the thermographic image;

determining positionally correctly assigned temperature profiles from the thermographic images, a temperature profile being a locally resolving profile, wherein different locations within the temperature profile are respectively assigned values of a measured variable representing the temperature at the respective location, and each positionally correctly assigned temperature profile being assigned to a same measuring region of the surface of the test object;

determining variations over time of temperature values from the temperature profiles for a large number of measuring positions of the measuring region that are recorded by the temperature profiles; and evaluating the variations over time based on at least one evaluation criterion indicative of the lateral heat flow in the measuring region.

2. The thermographic test method as claimed in claim 1, wherein, in the act of evaluating, at least one local maximum of the temperature values within the temperature profiles is sought.

3. The thermographic test method as claimed in claim 2, wherein, in the act of evaluating, a variation over time of an amplitude of temperature values in the region of the local maximum is evaluated.

4. The thermographic test method as claimed in claim 3, wherein, in the act of evaluating, a heat concentration value in the region of a local maximum of the temperature values within the temperature profiles is determined and a variation over time of the heat volume concentration value is evaluated.

5. The thermographic test method as claimed in claim 2, wherein, in the act of evaluating, a heat concentration value in the region of a local maximum of the temperature values within the temperature profiles is determined and a variation over time of the heat volume concentration value is evaluated.

6. The thermographic test method as claimed in claim 1, wherein, in the act of evaluating, at least three positionally correctly assigned temperature profiles are evaluated together.

7. The thermographic test method as claimed in claim 6, wherein between four and twenty positionally correctly assigned temperature profiles are evaluated together.

8. The thermographic test method as claimed in claim 4, wherein between four and twenty positionally correctly assigned temperature profiles are evaluated together.

9. The thermographic test method as claimed in claim 1, wherein, for testing an elongated test object, a relative movement is produced between the elongated test object and a recording device for recording the thermographic images in a direction of movement extending substantially parallel to a longitudinal direction of the elongated test object such that surface regions recorded by the thermographic images are offset with respect to one another in the direction of movement, the surface regions of the thermographic images recorded directly one after another overlapping in an overlapping region.

10. The thermographic test method as claimed in claim 9, wherein the recording device remains stationary and the elongated test object is moved relative to the recording device.

11. The thermographic test method as claimed in claim 10, further comprising the acts of:

analyzing a first thermographic image, recorded at a first point in time, of a series of thermographic images for the identification of at least a first picked-out image detail, which picked-out image detail contains a surface detail with a defect-like anomaly;

automatically finding a second image detail, corresponding to the first image detail, in a second thermographic image, recorded at a later, second point in time at a time interval from the first thermographic image; and evaluating thermographic data of the first image detail and the second image detail together, wherein a local maximum of the temperature values within the temperature profiles is sought if defect-like anomalies are identified.

12. The thermographic test method as claimed in claim 9, further comprising the acts of:

analyzing a first thermographic image, recorded at a first point in time, of a series of thermographic images for the identification of at least a first picked-out image detail, which picked-out image detail contains a surface detail with a defect-like anomaly;

automatically finding a second image detail, corresponding to the first image detail, in a second thermographic image, recorded at a later, second point in time at a time interval from the first thermographic image; and evaluating thermographic data of the first image detail and the second image detail together, wherein a local maximum of the temperature values within the temperature profiles is sought if defect-like anomalies are identified.

13. The thermographic test method as claimed in claim 11, wherein for the automatic finding, an expected position of the surface detail containing the defect-like anomaly in the second thermographic image is determined based on a relative speed between the elongated test object and the recording device, the direction of movement and the time that has passed between the first point in time and the second point in time; and wherein the relative speed is measured.

14. The thermographic test method as claimed in claim 12, wherein for the automatic finding, an expected position of the surface detail containing the defect-like anomaly in the second thermographic image is determined based on a relative speed between the elongated test object and the recording device, the direction of movement and the time that has passed between the first point in time and the second point in time; and wherein the relative speed is measured.

15. A thermographic testing device for locally resolving detection and identification of defects near a surface in a test object, the thermographic testing device comprising:

a heating device operatively configured to heat up a portion of the test object such that a thermal disequilibrium occurs between defective regions, affected by defects, and material of the test object that is free from defects, wherein a defect-free surrounding area of a defective region is not heated up or heated up less intensely than the defective region;

at least one recording device operatively configured to record a series of at least two thermographic images one after another at a time interval;

an evaluating device operatively configured to evaluate thermographic data of the at least two thermographic images; and wherein the testing device is operatively configured to carrying out the method as claimed in claim 1.

* * * * *